United States Patent [19]
Keenan et al.

[11] Patent Number: 5,612,357
[45] Date of Patent: Mar. 18, 1997

[54] USE OF COTININE TO ASSIST IN THE CESSATION OF TOBACCO SMOKING

[75] Inventors: Robert M. Keenan, Baltimore, Md.; Dorothy K. Hatsukami, Golden Valley, Minn.

[73] Assignee: Pharmaco Behavioral Associates, Inc., Minneapolis, Minn.

[21] Appl. No.: 293,585

[22] Filed: Aug. 22, 1994

Related U.S. Application Data

[63] Continuation-in-part of Ser. No. 885,314, May 18, 1992.
[51] Int. Cl.$^6$ ..................................................... A61K 31/44
[52] U.S. Cl. ........................... 514/343; 514/810; 514/813
[58] Field of Search .................................. 514/343, 810, 514/813

[56] References Cited

U.S. PATENT DOCUMENTS

| | | | |
|---|---|---|---|
| 2,981,641 | 4/1961 | O'Neill | 131/17 |
| 3,048,520 | 8/1962 | McKennis et al. | 167/65 |
| 3,867,519 | 2/1975 | Michaels | 424/19 |
| 3,870,791 | 3/1975 | Haddad et al. | 424/22 |
| 3,870,794 | 3/1975 | Hutchinson et al. | 514/343 |
| 4,051,842 | 10/1977 | Hazel et al. | 128/2.06 E |
| 4,136,177 | 1/1979 | Lin et al. | 424/211 |
| 4,140,122 | 2/1979 | Kuhl et al. | 128/260 |
| 4,255,415 | 3/1981 | Chrai et al. | 424/78 |
| 4,383,529 | 5/1983 | Webster | 604/20 |
| 4,621,074 | 11/1986 | Bourne | 514/12 |
| 4,668,506 | 5/1987 | Bawa | 424/429 |
| 4,713,244 | 12/1987 | Bawa et al. | 424/429 |
| 4,748,181 | 5/1988 | Hutchinson et al. | 514/343 |
| 4,788,063 | 11/1988 | Fisher et al. | 424/449 |
| 4,835,162 | 5/1989 | Abood | 514/305 |
| 4,931,279 | 6/1990 | Bawa et al. | 424/427 |
| 4,966,916 | 10/1990 | Abood | 514/534 |

FOREIGN PATENT DOCUMENTS

| | | |
|---|---|---|
| 273715 | 8/1962 | Australia . |
| 2428M | 3/1964 | France . |
| WO92/19241 | 11/1992 | WIPO . |

OTHER PUBLICATIONS

J.G. Liberto et al., "Cotinine in the Treatment of Cigarette Smoking," Poster Presented at the American Society for Addiction Medicine 8th National Conference on Nicotine Dependence, Toronto, Ontario, Canada, Oct. 14, 1995.

P. Jacob et al., "Disposition kinetics of nicotine and cotinine enantiomers in rabbits and beagle dogs," *J. Pharmaceutical Sciences*, 77, 396–400 (1988).

B. Kuo et al., "Influence of nicotine and cotinine on the expression of plasminogen activator activity in bovine aortic endothelial cells," *Thromb. Haemostasis*, 61, 70–79 (1989).

G. Kyerematen et al., "Disposition of nicotine and eight metabolites in smokers and nonsmokers: identification in smokers of two metabolites that are longer lived than nicotine," *Clin. Pharmacol. Ther.*, 48, 641–651 (1990).

W. Luck et al., "Extent of nicotine and cotinine transfer to the human fetus, placenta and amniotic fluid of smoking mothers," *Dev. Pharmacol. Ther.*, 8, 384–395 (1985).

C. Lynch et al., "Spontaneous cigarette brand switching: consequences for nicotine and carbon monoxide exposure," *Am. J. Public Health*, 78, 1191–1194 (1987).

R. C. O'Neill, "Tobacco products containing nicotine antagonists," *Chemical Abstracts*, 55, 16920 (1961).

E. Rylander et al., "Exposure to environmental tobacco smoke and urinary excretion of cotinine and nicotine in children," *Acta Poediatr. Scand.*, 78, 449–450 (1989).

I. Sasson et al., "Cigarette smoking and neoplasia of the uterine cervix: smoke constituients in cervical mucus," *New England J. Med.*, 312, 315–316 (1985).

K. Takada, et al., "Discriminitive stimulus effects of intravenous l-nicotine and nicotine analogs or metabolites on squirrel monkeys," *Psychopharmacology*, 99, 208–212 (1989).

B. Testa et al., "Circular Dichroic determination of the preferred conformation of nicotine and related chiral alkaloids in aqueous solution," *Mol. Pharmacol.*, 9, 10–16 (1973).

R. Barbieri et al., "Cotinine and nicotine inhibit human fetal adrenal 11β–hydroxylase," *J. Clin. Endocrinol. Metab.*, 69, 1221–1224 (1989).

A. H. Beckett et al., "A possible relationship between pKal and lipid solubility and the amounts secreted in urine to some tobacco alkaloids given to man," *J. Pharma. Pharmacol.*, 24, 115–120 (1972).

M. Curvall et al., "The pharmacokinetics of cotinine in plasma and saliva from non–smoking healthy volunteers," *Eur. J. Clin. Pharmacol.*, 38, 281–287 (1990).

M. Curvall et al., "Stimulation and evaluation of nicotine intake during passive smoking: cotinine measurements in body fluids of nonsmokers given intravenous infusions of nicotine," *Clin. Pharmacol. Ther.*, 47, 42–49 (1990).

J. Gabrielsson et al., "Constant–rate infusion of nicotine and cotinine. I. A physiological pharmacokinetic analysis of the cotinine disposition, and effects on clearance and distribution in the rat," *J. Pharmacokinetics Biopharmaceutics*, 15, 583–599 (1987).

R. Galeazzi et al., "Steady–stroke concentration of cotinine as a measure of nicotine–intake by smokers," *Eur. J. Clin. Pharmacol.*, 28, 301–304 (1985).

(List continued on next page.)

*Primary Examiner*—Kevin E. Weddington
*Attorney, Agent, or Firm*—Schwegman, Lundberg, Woessner & Kluth, P.A.

[57] ABSTRACT

A pharmaceutical composition is provided that is useful to alleviate various symptoms of tobacco withdrawal syndrome comprising an amount of cotinine or a pharmaceutically acceptable salt thereof in combination with a pharmaceutically acceptable carrier, which amount is effective to reduce or eliminate at least one of the symptoms of tobacco withdrawal syndrome in a human.

19 Claims, 8 Drawing Sheets

OTHER PUBLICATIONS

R. R. Hutchinson et al., "Effects of nicotine on avoidance, conditioned suppression and aggression response measures in animals and man," In: *Smoking Behavior: Motives and Incentives*, W. L. Dunn (ed.), V. H. Winston & Sons, Washington, D.C. pp. 171–196 (1973).

"Tobacco Products Containing Nicotine Antagonists", *Chemical Abstracts*, 55, col. 16920 (1961).

United States Department of Health and Human Services, *The Health Consequences of Smoking: Nicotine Addiction. A Report of the Surgeon General*, U.S. Govt. Print. Off., Washington D.C., DHHS Pub. No. (CDC) 88–8406, pp. 197–208 (1988).

T. Weiss et al., "Cotinine levels in follicular fluid and serum of IVF patients: effect on granulosa–luteal cell function in vitro", *Human Reproduction*, 4, 482–485 (1989).

K. Yamamoto et al., "Nicotine–Induced EEG and Behavioral Arousal", *Int. J. Neuropharmacol.*, 4, 359–373 (1965).

J. Yeh et al., "Nicotine and Cotinine Inhibit Rat Testis Androgen Biosynthesis In Vitro", *J. steroid Biochem.*, 33, 627–630 (1989).

P. Zeidenberg et al., Abstract of "Nicotine: Cotinine Levels in Blood During Cessation of Smoking", *Comp. Psychiatry*, 18, 93–111 (1977).

T. Patterson et al., "Nicotine and Cotinine Inhibit Steroidogenesis in Mouse Leydig Cells", *Life Sciences*, 46, 2650272 (1990).

C. Rahn et al., "Correlations Between Urinary Nicotine or Cotinine and Urinary Mutagenicity in Smokers on Controlled Diets", *Environ. Molec. Mutagenesis*, 17, 244–252 (1991).

M. Riebe et al., "Mutagenicity testing, in bacterial test systems, of some constituents of tobacco", *Mutation Research*, 101, 39–43 (1982).

M. Risner et al., "Effects of Nicotine, Cocaine and Some of Their Metabolites on Schedule–Controlled Responding by Beagle Dogs and Squirrel Monkeys", *J. Pharmacol. and Exp. Ther.*, 234, 113–119 (1985).

G. Scherer et al., "Pharmacokinetics of Nicotine, Cotinine and 3'–Hydroxycotinine in Cigarette Smokers", *Klin Wochenschr*, 66, 5–11 (1988).

S. Schwartz et al., "Studies on the Degradation of the Pyrrolidine Ring of (–)–Nicotine in Vivo", *J. Biol. Chem.*, 238, 1807–1812 (May 1963).

D. Sepkovic et al., "Biomedical Applications of Cotinine Quantitation in Smoking Related Research", *AJPH*, 75, 663–665 (Jun. 1985).

E. Srivastava et al., "Effect of Nicotine and Cotinine on the Production of Oxygen Free Radicals by Neutrophils in Smokers and Non–smokers", *Human Toxicology*, 8, 461–463 (1989).

S. Tiffany et al., "The development and initial validation of a questionnaire on smoking urges", *British J. of Addiction*, 86, 1467–1476 (1991).

J. Hughes et al., "Effects of Abstinence from Tobacco A Critical Review", *Research Advances in Alcohol and Drug Problems*, 10, 317–398 (1990).

K. Kim et al., "Effects of Some Nicotine Metabolites and Related Compounds on Isolated Smooth Muscle", *J. Pharm. Exper. Therapeutics*, 161, 59–69 (1968).

G. Kyerematen et al., "Time–Dependent Induction of Hepatic Drug Metabolism in Rats by Cotinine", *Life Sciences*, 32, 551–556 (1983).

E. LaVoie et al., "Evaluation of the Effects of Cotinine and Nicotine–N'–oxides on the Development of Tumors in Rats Initiated With N–[4–(5–Nitro–2–furyl)–2–thiazolyl]formamide", *J. Natl. Cancer Inst.*, 75, 1075–1081 (Dec. 1985).

W. Martin et al., "Physiologic, subjective, and behavioral effects of amphetamine, methamphetamine, ephedrine, phenmetrazine, and methylphenidate in man", *Clinical Pharmacology and Therapeutics*, 12, 245–258 (1971).

H. McKennis Jr. et al., "N–Methylation of Nicotine and Cotinine in Vivo", *J. Biol. Chem.*, 238, 719–723 (Feb. 1963).

H. McKennis Jr. et al., "Alternate Routes in the Metabolic Degradation of the Pyrrolidine Ring of Nicotine", *J. Biol. Chem.*, 239, 3990–3996 (Nov. 1964).

A. Meikle et al., "Nicotine and Cotinine Effects on 3Alpha Hydroxysteroid Dehydrogenase in Canine Prostate", *Life Sciences*, 43, 1845–1850 (1988).

D. Dawson et al., "Evaluation of the Developmental Toxicity of Nicotine and Cotinine with Frog Embryo Teratogenesis Assay: Xenopus", *Teratogenesis, Carcinogenesis and Mutagenesis*, 8, 329–338 (1988).

P. DeSchepper et al., "Kinetics of Cotinine After Oral and Intravenous Administration to Man", *Eur. J. Clin. Pharmacol.*, 31, 583–588 (1987).

P. Dominiak et al., "Effects of Nicotine and its Major Metabolites on Blood Pressure in Anaesthetized Rats", *Klin Wochenschr*, 63, 90–92 (1985).

N. Edwards et al., "Doxepin as an Adjunct to Smoking Cessation: A Double–Blind Pilot Study", *Am. J. Psychiatry*, 146, 373–376 (Mar. 1989).

W. Frankenburg et al., "The Chemistry of Tobacco Fermentation. I. Conversion of the Alkaloids. D. Identification of Cotinine in Fermented Leaves", *Cotinine in Fermented Tobacco Leaves*, 79, 149–151 (Jan. 5, 1957).

K. Fuxe et al., "On the Action of Nicotine and Cotinine on Central 5–Hydroxytryptamine Neurons", *Pharmacology, Biochem. & Behavior*, 10, 671–677 (1979).

S. Goldberg et al., "Nicotine and some related compounds: effects on schedule–controlled behaviour and discriminative properties in rats", *Psychopharmacology*, 97, 295–302 (1989).

D. Hatsukami et al., "Effects of Nicotine Gum on Prevalence and Severity of Withdrawal in Female Cigarette Smokers", *J. Substance Abuse*, 3, 427–440 (1991).

J. Hughes et al., "Signs and Symptoms of Tobacco Withdrawal", *Archives of Genera Psychology*, 43, 289–294 (1986).

N. Benowitz, "The Use of Biologic Fluid Samples in Assessing Tobacco Smoke Consumption", *Measurement in the Analysis and Treatment of Smoking Behavior*, J. Grabowski et al. eds., NIDA Research Monograph No. 48, U.S. DHHS, PHS, Adamha (1983).

N. Benowitz et al., "Cotinine disposition and effects", *Clin. Pharmacol. Ther.*, 34, 604–611 (Nov. 1983).

N. Benowitz et al., "Inverse Relation Between Serum Cotinine Concentration and Blood Pressure in Cigarette Smokers", *Circulation*, 80, 1309–1312 (Nov. 1989).

J. Borzelleca et al., "Studies on the Respiratory and Cardiovascular Effects of (–)–Cotinine", *J. Pharm. Exper. Therapeutics*, 137, 313–318 (1962).

E. Bowman et al., "(–)–Cotinine", *Biochem. Preparations*, 10, 36–39 (1963).

E. Bowman et al., "Studies on the Metabolism of (–)–Cotinine in the Human", *J. Pharmacol. Exp. Ther.*, 135, 306–311 (1962).

E. Bowman et al., "Disposition and Fate of (−)-Citubube–H3 in the Mouse", *J. Pharmac. Exper. Therapeutics,* 143, 301–308 (1964).

M.E. Carroll et al., "Nicotine Dependence in Rats", *Life Sci.,* 45 1381–1388 (1989).

R. Chahine et al., "The in vitro Effects of Nicotine and Cotinine on Prostacyclin and Thromboxane Biosynthesis", *Prostaglandins, Leukotrienes, and Essential Fatty Acids,* 40, 261–266 (Aug. 1990).

M. Curvall et al., Abstract of "Monitoring absorption by means of determination of nicotine and cotinine", *Arch. Toxicol. Suppl.,* 9, 88–102 (1986).

L. Abood et al., "Specific Binding and Metabolism of (−)-and (+)-[3H]-Nicotine in Isolated Rat Hepatocytes and Hepatocyte Membranes", *Arch. Int. Pharmacodyn,* 273, 62–73 (1985).

American Psychiatric Assoc., *Diagnostic and Statistical Manual of Mental Disorders,* Washington D.C., 159–160, 176–178 (3rd ed. 1980).

R. Barbieri et al., "Nicotine, Cotinine and Anabasine Inhibit Aromatase in Human Trophoblast in Vitro", *J. Clin. Invest.,* 77, 1727–1733 (Jun. 1986).

R. Barbieri et al., "The Effects of Nicotine, Cotinine, and Anabasine on Rat Adrenal 11–beta–hydroxylase and 21–hydroxylase", *J. Steroid Biochem.,* 28, 25–28 (1987).

1. RATE THOSE SYMPTOMS WHICH YOU ARE EXPERIENCE RIGHT NOW.

| | NONE | SLIGHT | MILD | MODERATE | SEVERE |
|---|---|---|---|---|---|
| A. CRAVING FOR CIGARETTES | 0 | 1 | 2 | 3 | 4 |
| B. IRRITABILITY | 0 | 1 | 2 | 3 | 4 |
| C. ANXIETY | 0 | 1 | 2 | 3 | 4 |
| D. DIFFICULTY CONCENTRATING | 0 | 1 | 2 | 3 | 4 |
| E. RESTLESSNESS | 0 | 1 | 2 | 3 | 4 |
| F. INCREASED APPETITE | 0 | 1 | 2 | 3 | 4 |
| G. DEPRESSED MOOD | 0 | 1 | 2 | 3 | 4 |
| H. IMPATIENCE | 0 | 1 | 2 | 3 | 4 |

FIG. 1

12.
USE OF COTININE TO ASSIST IN THE CESSATION OF TOBACCO SMOKING

CROSS-REFERENCE TO RELATED APPLICATION

This application is a continuation-in-part of U.S. patent application Ser. No. 07/885,314, filed May 18, 1992, which is incorporated by reference herein.

BACKGROUND OF THE INVENTION

Cigarette smoking continues to be the major preventable cause of death in the United States resulting in nearly 400,000 deaths per year due to cancer and heart disease. Despite the potential adverse health effects, grave consequences, the vast majority of cigarette smokers are unable to cease smoking.

The lack of smoking cessation success is thought to be related to the tobacco withdrawal syndrome or tobacco abstinence syndrome that most smoker experience during their attempts to quit. See, Office of Smoking and Health, *The Health Consequences of Smoking: Nicotine Addiction. A Report to the Surgeon General*, U.S. Govt. Print. Off., Washington, D.C., DHHS Pub. No. (CDC) 88–8406 (1988). The most common effects are similar to those in almost all abstinence syndromes, and include decreased heart rate, anxiety, difficulty concentrating, impatience, irritability and restlessness. See, American Psychiatric Assoc., *Diagnostic and Statistical Manual*, Washington D.C. (3rd ed. 1980) at pages 159–160, 176–178. Most withdrawal effects occur within 24 hours, peak in the first 1–2 weeks and significantly decrease at one month. It is widely believed that the effects of abstinence from tobacco are due to nicotine deprivation, and that abstinence effects from smoking prevent smokers from stopping. See, J. R. Hughes et al., in *Research and Advances in Alcohol and Drug Problems*, Vol. 10, L. T. Kozlowski et al., eds., Plenum Pub. Corp. (1990) at pages 317–398.

Of the pharmacological approaches to aiding cessation of smoking nicotine replacement, e.g., via transdermal nicotine patches or nicotine gum is the most widely used. Nicotine gum decreases abstinence discomfort, especially anxiety, decreased memory and irritability. On the other hand, nicotine gum does not reliably decrease weight gain or craving. Also, discontinuing use of nicotine gum leads to some of the same symptoms as the cigarette withdrawal syndrome. Furthermore, nicotine is toxic, and the availability of nicotine gum or patches poses a risk of poisoning to children and pets.

Other studies have demonstrated that alpha-2 agonists, such as clonidine, decrease postcessation anxiety, irritability and difficulty concentrating. Decreased sympathetic activity has been postulated to be the mechanism by which these drugs decrease abstinence effects. Although tobacco abstinence has some effects that could be attributed to sympathetic activity, it lacks the typical signs and symptoms of sympathetic overactivity, such as tachycardia, diaphoresis and hypertension. Thus, the mechanism by which alpha-2 agonists exert their effects is unclear.

Presently, Dynagen, Inc., published PCT application WO/92/19241 disclosed drug delivery systems said to deliver a controlled, sustained release of lobeline for the treatment of nicotine dependency. While a number of other pharmacological treatments, such as use of doxepin, ACTH, and corticotrophins, for abstinence symptoms have been tested, none of the studies reported baseline and postcessation values for abstinence symptoms. See, for example, S. J. Bourne (U.S. Pat. No. 4,621,074).

Therefore, a continuing need exists for pharmacological treatments that will facilitate smoking cessation, e.g., by blocking or relieving tobacco withdrawal syndrome, or reducing the symptoms of nicotine withdrawal.

SUMMARY OF THE INVENTION

The present invention provides a therapeutic method of treatment to (a) alleviate symptoms of the tobacco withdrawal syndrome (TWS), or (b) alleviate the similar abstinence effects due to cessation of nicotine alone, comprising administering to a human in need of such treatment, i.e., a smoker or abstinent smoker, an amount of cotinine or a pharmaceutically acceptable salt thereof, in an amount effective to significantly reduce or eliminate at least one of the symptoms of TWS or of nicotine withdrawal. As discussed above, the symptoms of both tobacco and nicotine withdrawal are similar and are art recognized to include craving for nicotine, depressed mood, anxious/tense, irritable/angry, impatience, restlessness, difficulty concentrating, increased eating, weight gain and drowsiness. See FIG. 1. The present method is effective both to alleviate the TWS acutely and to permit patients to maintain abstinence from nicotine for extended periods of time.

In a preferred embodiment, the present invention also provides a therapeutic method to alleviate the craving for cigarettes, tobacco and/or nicotine that is associated with cessation of tobacco or nicotine use, e.g., by chewing or smoking, by the administration of an effective amount of cotinine or a pharmaceutically acceptable salt thereof, to a human in need of such treatment. However, the present invention is also useful to treat the symptoms of nicotine withdrawal which are due, for example, to cessation of use of nicotine gum or a nicotine transdermal patch.

The present invention is exemplified by a study in which (−)cotinine base was orally administered to abstinent cigarette smokers in a double-blind placebo controlled study. The results of this study demonstrate that: (1) cotinine fumarate up to at least 160 mg is safe, (2) cotinine fumarate at the 80 mg dose suppresses specific withdrawal symptoms, and (3) at the 40 and 80 mg dose, cotinine fumarate suppresses total withdrawal discomfort. These effects occur at doses of cotinine which do not cause significant effects on heart rate and blood pressure.

Cotinine has many qualities which can enhance its value as a smoking cessation aid. Cotinine has a long in vivo half-life, complete oral bioavailability, minimal effect on the cardiovascular system, and has not been reported to be harmful even at very high doses in many species including man. Also, became cotinine has no significant effect on the heart, a combined pharmacologic treatment approaching cotinine and nicotine may be possible.

The present invention also provides an article of manufacture comprising packaging material, such as a box, bottle, tube, sprayer, insufflator, intravenous (i.v.) bag, envelope and the like; and at least one unit dosage form of a pharmaceutical agent contained within said packaging material, wherein said pharmaceutical agent comprises cotinine or a pharmaceutically acceptable salt thereof in an amount effective to alleviate the tobacco withdrawal syndrome or the symptoms of nicotine withdrawal, and wherein said packaging material includes instruction means which indicate that said cotinine or said pharmacologically acceptable salt thereof can be used for alleviating tobacco withdrawal syndrome, or the symptoms of nicotine withdrawal. Suitable instruction means include printed labels, printed package inserts, tags, cassette tapes, and the like.

BRIEF DESCRIPTION OF THE FIGURES

FIG. 1 depicts the Minnesota Withdrawal Symptom Checklist.

DETAILED DESCRIPTION OF THE INVENTION

Cotinine

Figure 2:
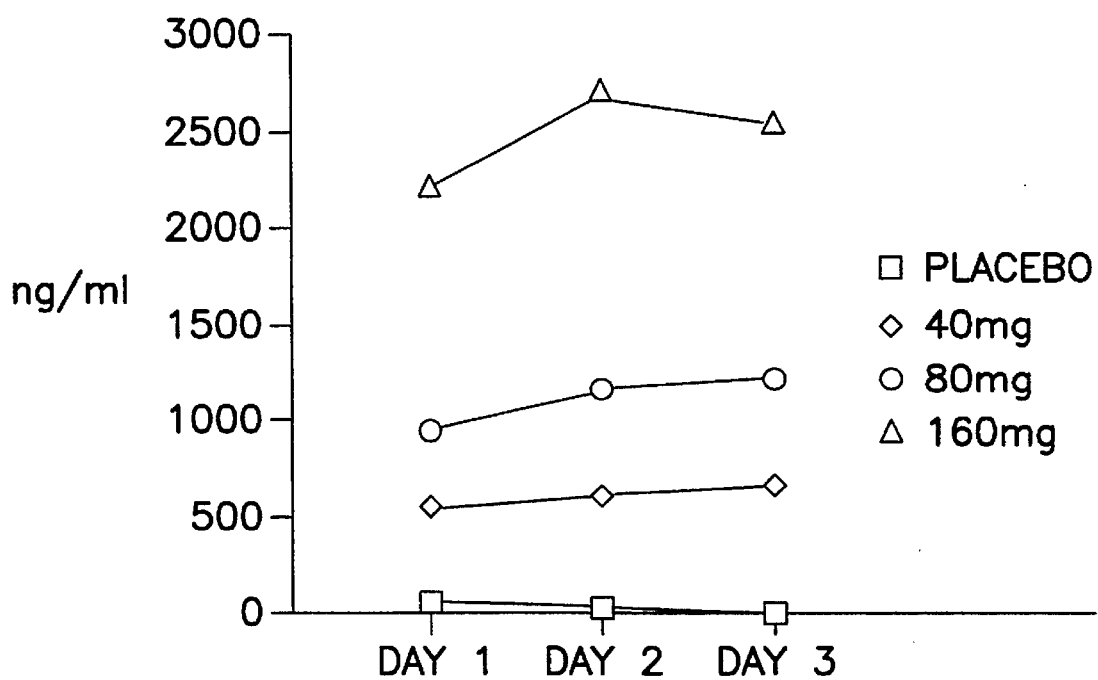
FIG. 2 is a graph depicting mean blood cotinine levels of the test subjects.
Figure 3:
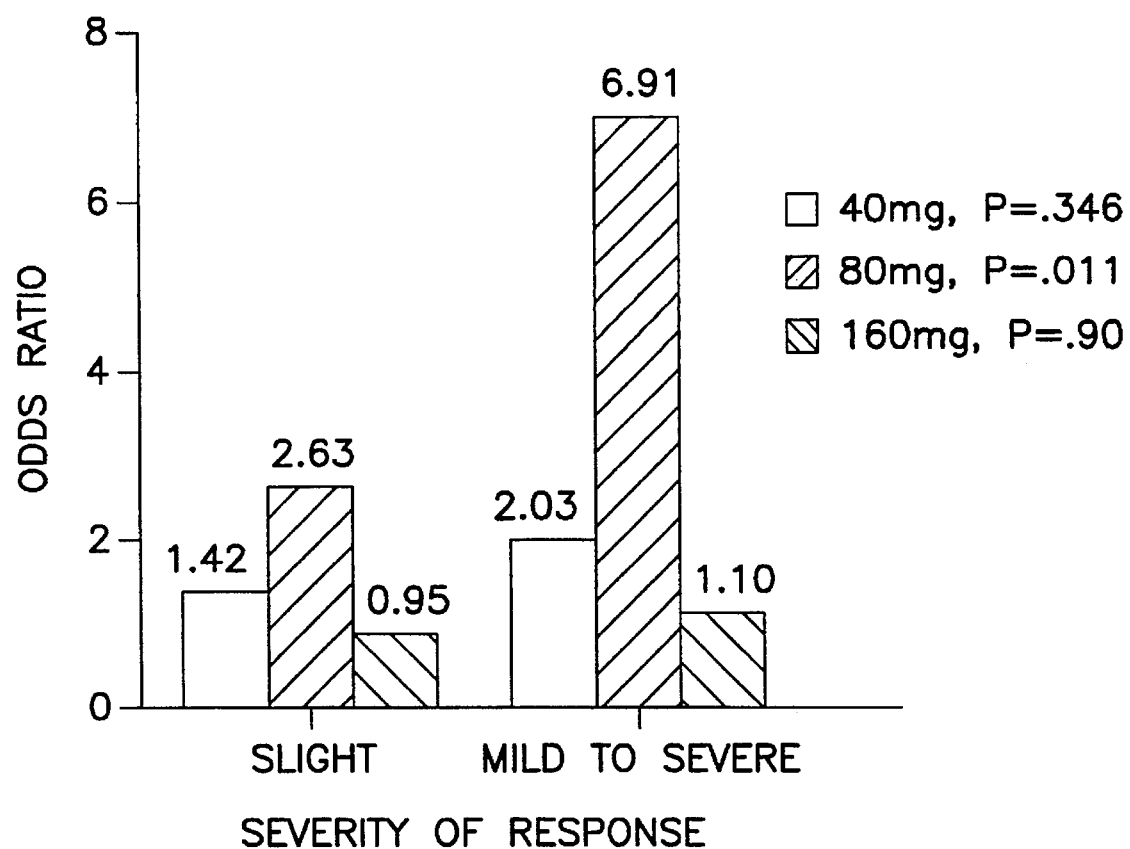
FIG. 3 is a graph depicting the odds ratio of no irritability to severity by dosage.
Figure 4:
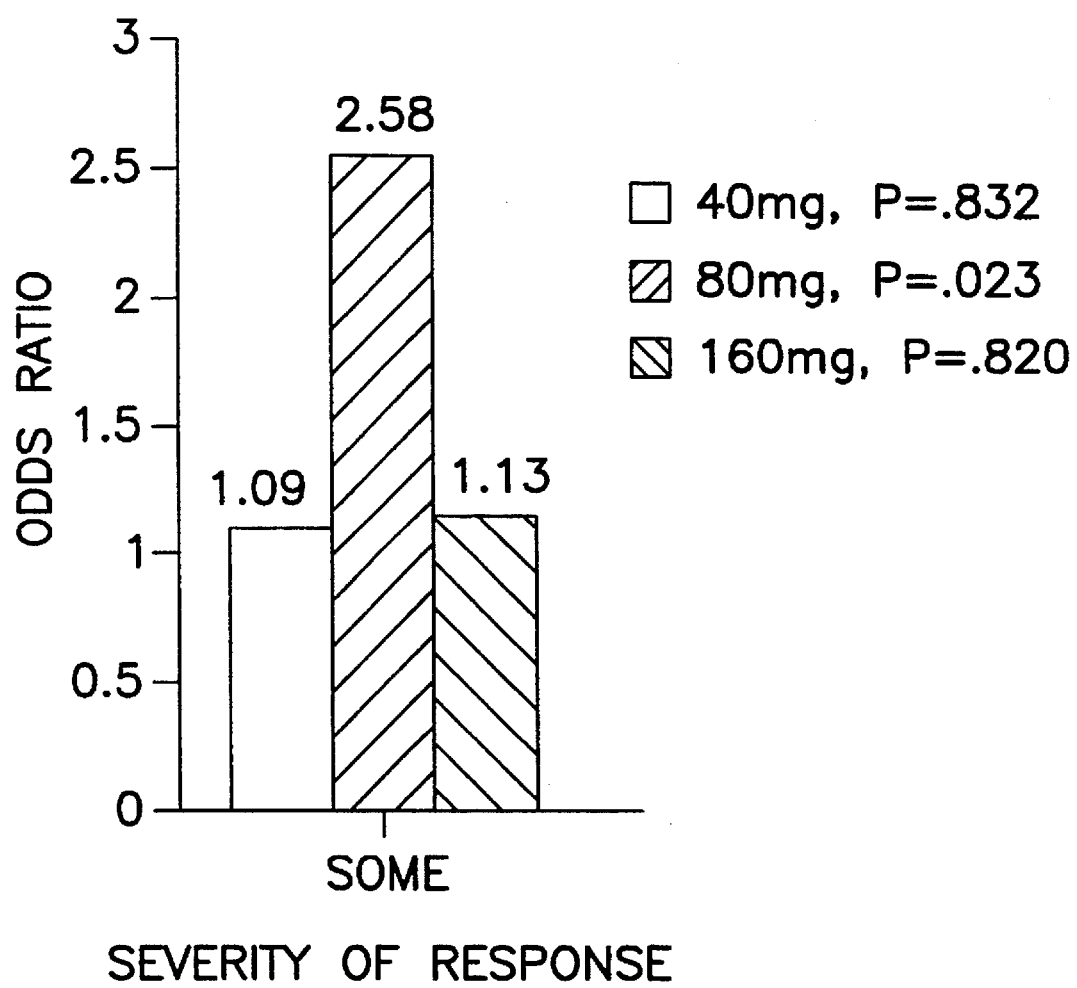
FIG. 4 is a graph depicting the odds ratio of no anxiety to some anxiety by dosage.
Figure 5:
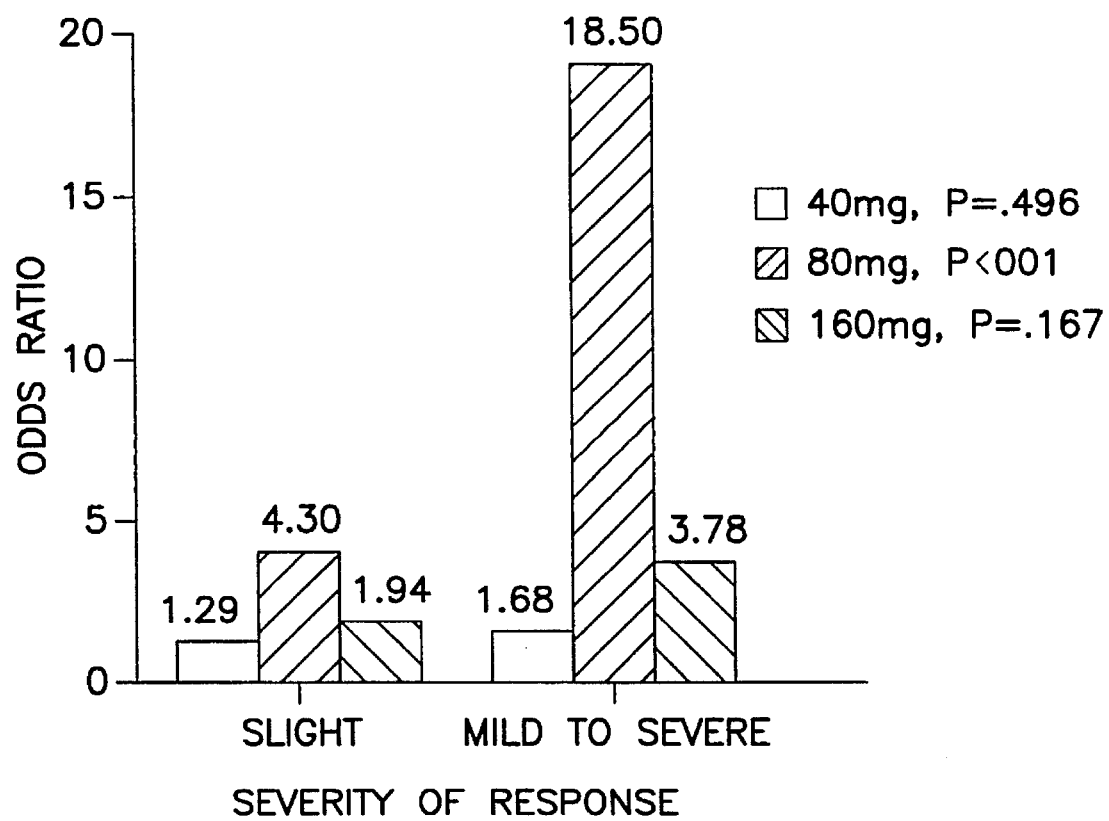
FIG. 5 is a graph depicting the odds ratio of no difficulty concentrating to level experienced.
Figure 6:
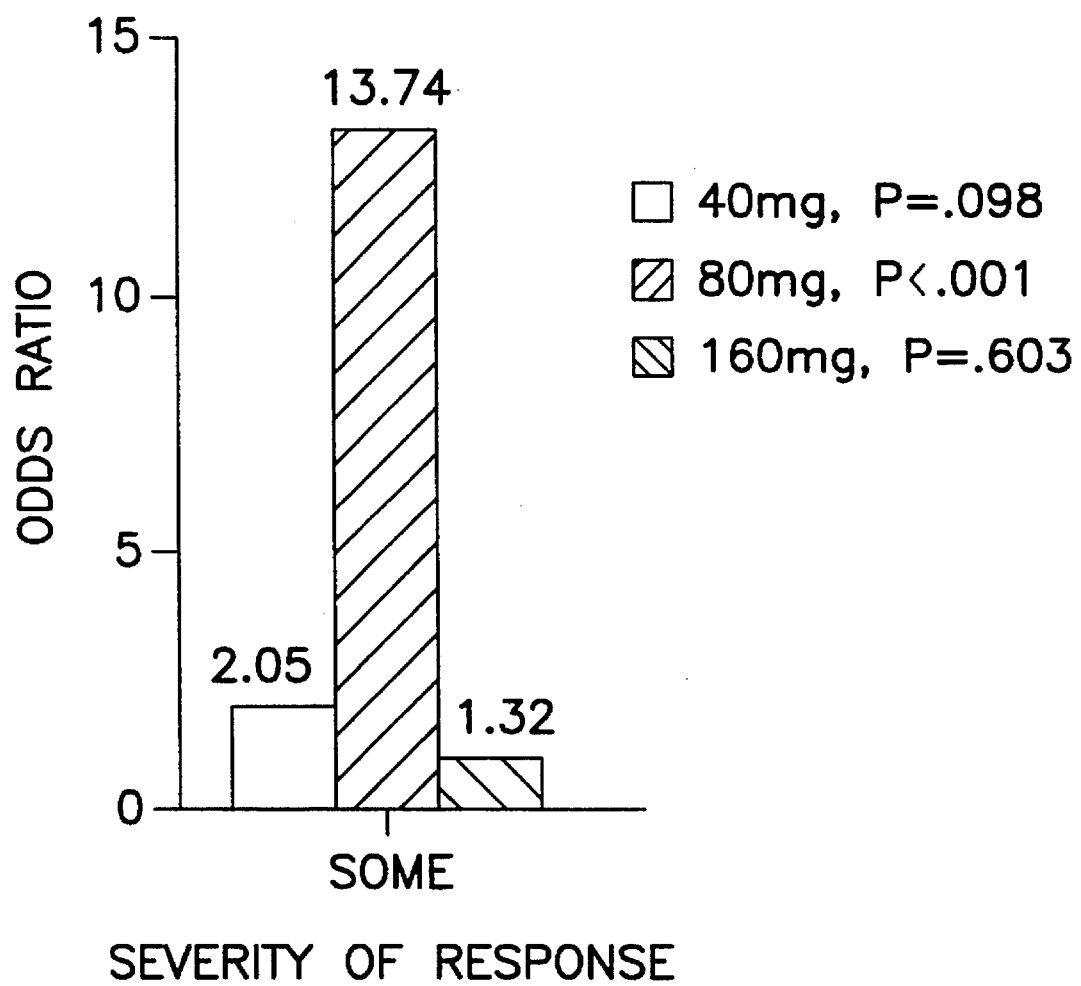
FIG. 6 is a graph depicting odds of experiencing no impatience to some impatience.
Figure 7:
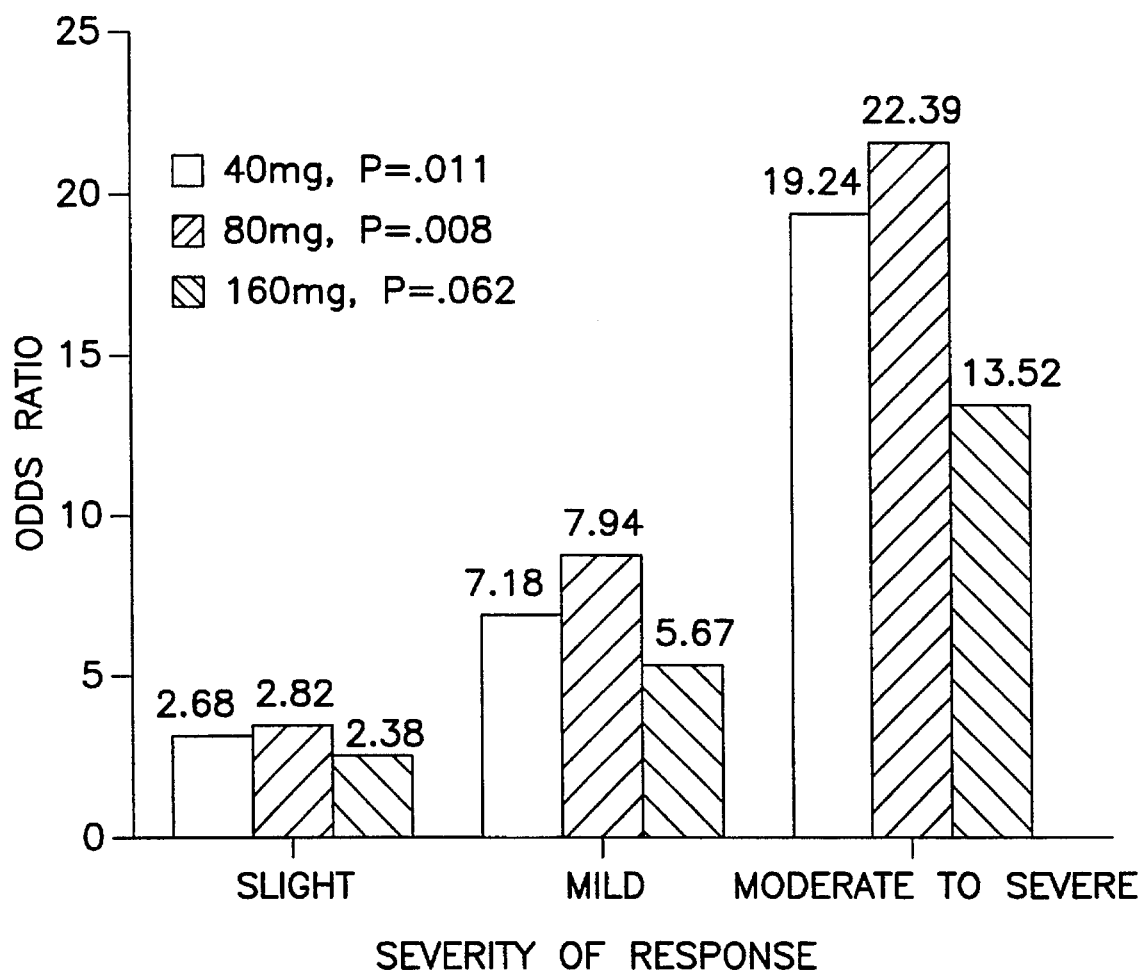
FIG. 7 is a graph depicting odds ratio of no increased appetite to level experienced.

Cotinine (1-methyl-5-(3-pyridinyl)-2-pyrrolidinone) has the formula shown below:

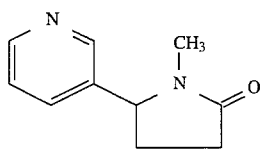

The physiologically active form is the (−)-isomer, so as used herein, the term "cotinine" includes (−)-cotinine, or the racemic form, (+)-cotinine. The free base, depicted above, can be employed in the practice of the invention, as can the pharmaceutically acceptable salts. These include the amine-acid addition salts of nontoxic or organic acids or inorganic acids, such as the tartarate, fumarate ("scotine"), citrate, maleate, malate, hydrobromide, hydrochloride, sulfate, phosphate and the like. For example, see F. Vaitekunas, *J. Amer. Chem. Soc.*, 79, 149 (1957). E. R. Bowman et al., in *J. Pharmacol. and Exp. Ther.*, 135, 306 (1962) report the preparation of (−)-cotinine free base from (−)-nicotine. The preparation and purification of (−)-cotinine fumarate is described by N. L. Benowitz et al., *Clin. Pharmacol. Ther.*, 34, 604 (1983).

Cotinine is the major metabolite of nicotine which accumulates in the body as a result of nicotine exposure and has previously been believed to be pharmacologically inactive. For example, see N. L. Benowitz, "The use of biologic fluid samples in assessing tobacco smoke consumption", in *Measurement in the Analysis and Treatment of Smoking Behavior*, J. Grabowski et al., eds., NIDA Research Monograph No. 48, U.S. DHHS, PHS, ADAMHA (1983). In contrast to nicotine, cotinine has a relatively long terminal elimination half-life (two versus sixteen hours, respectively). Due to this pharmacological characteristic, cotinine has become the principally used objective biochemical marker of nicotine exposure in cigarette smoking and/or cessation-related research paradigms.

While cotinine is a well-known metabolite of nicotine and is routinely measured in many laboratories, no systematic investigation of the physiological and subjective effects produced by intravenous cotinine administration has been performed in humans. K. I. Yamamoto et al., *International J. Neuropharmacol.*, 4, 359 (1965) reported that intravenous cotinine produced increases only slightly in EEG activity and behavioral arousal in cats with only a slight decrease in blood pressure. In squirrel monkeys, intramuscular cotinine injections increased rates of responding on fixed interval schedules of reinforcement over a wide range of doses (M. E. Risner et al., *J. Pharmacol. and Exp. Ther.*, 234, 113 (1985); S. R. Goldberg et al., *Psychopharmacology*, 97, 295 (1989)). These findings, taken together, suggest that cotinine is behaviorally active. However, the pharmacologic mechanism of action has yet to be determined.

In two recent human studies, the pharmacokinetic profiles of intravenous and orally administered cotinine were examined without emphasis on measuring the subjective and/or physiological changes induced by this compound (N. L. Benowitz et al., *Clin. Pharmacol. and Therapeutics*, 34, 604 (1983); P. J. DeSchepper et al., *Eur. J. Pharmacol.*, 31, 583 (1987)). Moreover, using an uncontrolled experimental design, Benowitz et al., *Clin. Pharm. and Ther.*, 34, 604 (1988), found that intravenous cotinine infusion over 60 min. produced no cardiovascular changes and significant decreases in subjective ratings of desire to smoke, irritability, low energy and anxiety/tension. These changes were comparable to placebo-induced changes found in other experiments with nicotine. Using a rapid infusion of cotinine over 5 minutes, no significant changes in the subjective ratings were observed. Consequently, Benowitz and his colleagues concluded that cotinine lacked significant pharmacologic activity in humans.

Administration and Dosages

While it is possible that, for use in therapy, cotinine and/or its salts may be administered as the pure chemicals, as by inhalation of a free powder via an insufflator, it is preferable to present the active ingredient as a pharmaceutical formulation. The invention thus further provides a pharmaceutical formulation comprising cotinine and/or a pharmaceutically acceptable salt thereof, together with one or more pharmaceutically acceptable carriers therefor and, optionally, other therapeutic and/or prophylactic ingredients. The carrier(s) must be 'acceptable' in the sense of being compatible with the other ingredients of the formulation and not deleterious to the recipient thereof.

Pharmaceutical formulations include those suitable for oral or parenteral (including intramuscular, subcutaneous and intravenous) administration. Forms suitable for parenteral administration also include forms suitable for administration by inhalation or insufflation or for nasal, or topical (including buccal, rectal, vaginal and sublingual) administration. The formulations may, where appropriate, be conveniently presented in discrete unit dosage forms and may be prepared by any of the methods well known in the art of pharmacy. Such methods include the step of bringing into association the active compound with liquid carriers, solid matrices, semi-solid carriers, funely divided solid carriers or combinations thereof, and then, if necessary, shaping the product into the desired delivery system.

Pharmaceutical formulations suitable for oral administration may be presented as discrete unit dosage forms such as hard or soft gelatin capsules, cachets or tablets each containing a predetermined amount of the active ingredient; as a powder or as granules; as a solution, a suspension or as an emulsion; in a chewable base such as a synthetic resin or chicle for ingestion of the cotinine from a chewing gum. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art, i.e., with enteric coatings.

Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds according to the invention may also be formulated for parenteral administration (e.g., by injection, for example, bolus injection or continuous infusion) and may be presented in unit dosage form in ampules, prefilled syringes, small volume infusion containers or multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

For topical administration to the epidermis, the cotinine may be formulated as ointments, creams or lotions, or as the active ingredient of a transdermal patch. Suitable transdermal delivery systems are disclosed, for example, in A. Fisher et al. (U.S. Pat. No. 4,788,603), or R. Bawa et al. (U.S. Pat. Nos. 4,931,279; 4,668,506; and 4,713,224). Ointments and creams may, br example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredient can also be delivered via iontophoresis, e.g., as disclosed in U.S. Pat. Nos. 4,140,122; 4,383,529; or 4,051,842.

Formulations suitable for topical administration in the mouth include unit dosage forms such as lozenges comprising active ingredient in a flavored base, usually sucrose and acadia or tragacanth; pastilles comprising the active ingredient in an inert base such as gelatin and glycerin or sucrose and acacia; mucoadherent gels, and mouthwashes comprising the active ingredient in a suitable liquid carrier.

When desired, the above-described formulations can be adapted to give sustained release of the active ingredient employed, e.g., by combination with certain hydrophilic polymer matrices, e.g., comprising natural gels, synthetic polymer gels or mixtures thereof.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping in molds.

Formulations suitable for vaginal administration may be presented as pessaries, tampons, creams, gels, pastes, foams or sprays containing, in addition to the active ingredient, such carriers as are known in the art to be appropriate.

For administration by inhalation, the compounds according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoromethane, carbon dioxide or other suitable gas. In the case of a pressurized aerosol, the dosage unit may be determined by providing a valve to deliver a metered amount.

Alternatively, for administration by inhalation or insufflation, the compounds according to the invention may take the form of a dry powder composition, for example, a powder mix of the compound and a suitable powder base such as lactose or starch. The powder composition may be presented in unit dosage form in, for example, capsules or cartridges or, e.g., gelatin or blister packs from which the powder may be administered with the aid of an inhalator or insufflator.

For intra-nasal administration, the compounds of the invention may be administered via a liquid spray, such as via a plastic bottle atomizer. Typical of these are the Mistometer® (Wintrop) and the Medihaler® (Riker).

For topical administration to the eye, the cotinine can be administered as drops, gels (see, S. Chrai et al., U.S. Pat. No. 4,255,415), gums (see S. L. Lin et al., U.S. Pat. No. 4,136,177) or via a prolonged-release ocular insert (see A. S. Michaels, U.S. Pat. No. 3,867,519) and H. M. Haddad et al., U.S. Pat. No. 3,870,791).

The pharmaceutical compositions according to the invention may also contain other adjuvants such as flavorings, colorings, antimicrobial agents, or preservatives.

It will be further appreciated that the amount of cotinine, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 1 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day, calculated as (−)-cotinine in the free base form.

The compound is conveniently administered in unit dosage form; for example, containing 5 to 1000 mg, conveniently 10 to 750 mg, most conveniently, 40–50 to 100–500 mg of active ingredient per unit dosage form.

Ideally, the active ingredient should be administered to achieve peak plasma concentrations of the active compound of from about 0.5 to about 75 $\mu M$, preferably, about 1 to 50 $\mu M$, most preferably, about 2 to about 30 $\mu M$. This may be achieved, for example, by the intravenous injection of a 0.05 to 5% solution of the active ingredient, optionally in saline, or orally administered as a bolus containing about 1–100 mg, preferably about 25–95 mg of the active ingredient. Desirable blood levels may be maintained by continuous infusion to provide about 0.01–5.0 mg/kg/hr or by intermittent infusions containing about 0.4–15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The invention will be further described by reference to the following detailed Example.

EXAMPLE I

Oral Administration of (−)-Cotinine Fumarate

To investigate the effects of oral cotinine on the symptoms of the tobacco withdrawal syndrome (TWS) as experienced by abstinent smokers, under controlled conditions, the following double blind, placebo controlled study was conducted at the University of Minnesota. More specifically, the study was conducted to (1) determine the safety of various doses of cotinine fumarate; (2) determine blood cotinine concentrations attained from various doses of cotinine fumarate; and (3) determine effects of various doses of cotinine fumarate on withdrawal signs and symptoms including physiological and subjective symptoms. Preliminary analysis of the data from this study demonstrate the: (1) cotinine fumarate up to 160 mg is safe, (2) cotinine fumarate at the 80 mg dose suppresses specific withdrawal symptoms, and (3) at the 40 and 80 mg dose, cotinine fumarate suppresses total withdrawal discomfort. These effects occur at doses of cotinine which do not cause effects on heart rate and blood pressure.

Methods

A. Subjects: Subjects (N=37 male and female smokers) were recruited from the Minneapolis/St. Paul metropolitan area via newspaper advertisements. Subjects were initially screened over the telephone. If they met the telephone screening criteria, then they were seen by the research coordinator and physician. At this screening session, informed consent was obtained. Subjects were required to complete a smoking history and Fagerstrom Nicotine Tolerance Questionnaire. In addition, an alveolar carbon monoxide sample and blood samples to measure cotinine and nicotine levels were obtained. The physician then obtained a medical and concomitant medication history and conducted a physical examination that included a 12-lead electrocardiogram (ECG) and laboratory screening of blood and urine specimens. Subjects were included if they: (a) smoked at least one pack of cigarettes/day for at least one year; (b) submitted a CO>10 ppm; and (c) were in good health (e.g., no history of myocardial infarction, angina pectoris, sustained or episodic cardia arrhythmias, symptomatic peripheral vascular disease) as verified by medical history, screening examination, and screening laboratory tests. Subjects were excluded if they: (a) required any form of regular psychotropic medication; (b) chronically used systemic steroids or antihistamines; (c) abused alcohol or any other recreational or prescription drug; (d) used any other tobacco products including smokeless tobacco. To maximize compliance and completion of the study, subjects were paid $700 for their participation.

B. Procedure: This study used a between-subject design with one of the doses of cotinine or placebo as the across subject variable. The study was run at the University of Minnesota General Clinical Research Center, Minneapolis, Minn. U.S.A., a federally funded inpatient research ward. Total participation in this study was 10 days. See Table 1 for experimental procedures.

TABLE 1

| Experimental Procedure | | |
|---|---|---|
| Cue Exposure | Cue Exposure | Cue Exposure |
| 1  2  3 | 4  5  6 | 7  8  9  10 |
| Ad Lib  Placebo  Cotinine | | Placebo  Discharge |

Subjects were admitted to research ward at noon. During the first two days of the study, baseline measure were obtained while the subject smoked cigarettes on an ad libitum basis. Subjects were required to be abstinent from cigarettes beginning in the rooming of the third day. All subjects were given placebo at this time to allow some clearance of nicotine. On the morning of the fourth day, subjects were given placebo or one of the following oral doses of cotinine fumarate: 40 mg, 80 mg, and 160 mg. Nine subjects were to be run per each condition. Doses of cotinine were tested in ascending order. The subjects who are assigned to placebo were interspersed across the active dose conditions so that the blind would be maintained. If no adverse effects were detected for a particular dose, then the next higher dose was tested with the next group of subjects. Subjects were given one of the oral doses of cotinine fumarate/placebo for the next 3 days. Three days of cotinine dosing were chosen since the maximum tobacco withdrawal effects are observed during 24–72 hours of abstinence. See Hughes et al., *Res. Adv. in Alcohol & Drug Problems*, 10, Kozlowski et al., eds., Plenum Pub. (1990) at pages 317–398. Beginning on the eighth day, all subjects were required to take placebo again for three more days. This placebo condition would allow observation of withdrawal signs and symptoms from cotinine fumarate. To minimize experimenter bias, the investigators and nurses involved with assessment, however, were led to believe that subject during this placebo phase were randomly assigned to continue to take the medication given to them prior three days or assigned to placebo. Subjects were discharged in the morning of the tenth day if medical and psychological status were considered normal.

Abstinence was confirmed by biochemical verification (e.g., alveolar carbon monoxide) obtained at random times three times/day, evenly distributed across the day. Weight (after voiding) in the hospital gown was recorded and a sleep scale completed every rooming. See Table 2.

TABLE 2

| NICOTINE METABOLITE STUDY - TEST CHECKLIST | | | | | | | | | |
|---|---|---|---|---|---|---|---|---|---|
| TEST | DAYS TESTED | 0630 | 0830 | 0930 | 1000 | 1200 | 1500 | 1800 | 2100 |
| PHYSICAL TESTING | | | | | | | | | |
| WEIGHT | PE, D0–10 | X | | | | | | | |
| BLOOD PRESSURE | PE, D0–10 | | X | X | X | X | X | X | X |
| HEART RATE | PE, D0–10 | | X | X | X | X | X | X | X |
| SKIN TEMPERATURE | DAY 1–9 | | X | | X | X | X | | |
| EKG | PE, D1–9 | | X | | | X | | | |
| PSYCH TESTING | | | | | | | | | |
| MWSC- MN.W/DRAWAL SX. CHECKLIST | DAY 1–9 | | X | | X | X | X | | |
| POMS | DAY 1–9 | | X | | X | X | X | | |
| VISUAL ANALOG SCALE | DAY 1–9 | | X | | X | X | X | | |
| VISUAL ANALOG SCALE- DRUG EFFECTS | DAY 3–9 | | X | | X | X | X | | |

TABLE 2-continued

NICOTINE METABOLITE STUDY - TEST CHECKLIST

| TEST | DAYS TESTED | 0630 | 0830 | 0930 | 1000 | 1200 | 1500 | 1800 | 2100 |
|---|---|---|---|---|---|---|---|---|---|
| ADDICTION RESEARCH CENTER INVENTORY | DAY 1-9 | | X | | X | X | X | | |
| ADVERSE EFFECTS | DAY 1-9 | | X | | X | X | X | | |
| QUESTIONNAIRE OF SMOKING URGES | DAY 1-9 | | X | | X | X | X | | |
| RECORD OF OBSERVED W/DRAWAL SX'S | DAY 1-9 | | X | | X | X | X | | |
| SLEEP DIARY | DAY 1-10 | | X | | | | | | |

Subjects were required to complete subjective measures at the same times in the morning and afternoon throughout the study. See Table 2. These measures included the Addiction Research Center Inventory (Martin, Sloan, Sapira and Jasinski, Clin. Pharmacol. Ther., 1, 245 (1971)) which measures drug-like effects; the Profile of Mood States (McNair et al., Manual Profile of Mood States, San Diego Educational and Industrial Testing Service (1971)) which measures various moods such as depression-dejection, tension-anxiety, confusion, anger-hostility, vigor and fatigue; a VAS (which measures nicotine-like effects as well as how much an individual likes cotinine); the modified Minnesota Withdrawal Symptom Checklist (see FIG. 1; Hughes and Hatsukami, Arch. of Gen. Psychol., 43, 289 (1986)) comprised symptoms of nicotine withdrawal as described in the DMS-IV (APA, 1994) which subjects rated on a 0 to 4 scale with 0=none, 1=slight, 2=mild, 3=moderate, 4=severe; and the Smoking Urges Questionnaire (Tiffany & Drobes, Brit. J. Addiction, 86, 1467 (1991)) which measured two factors, one reflecting intention, desire and anticipation to smoke, and the other factor reflecting anticipation of relief from negative affect, nicotine withdrawal and urgent or overwhelming desire to smoke.

Subjects were also measured at these times for vitals (sitting and standing blood pressure and heart rate), skin temperature, respiratory rate, assessed for adverse events, and a 12-lead EKG was obtained. Caloric intake was carefully monitored throughout the study. Meals, similar to ones normally ingested by the subjects, were planned by the registered dietician who then supervised the careful measurement and preparation of all the foods eaten by the subjects. Meal and snack trays (foods of various macronutrients made available to the subjects all day) were returned to the kitchen where all uneaten food and beverages were remeasured after each meal, thereby all the eaten food was recorded by type and amount. Food content was later analyzed and calculated for daily amount of carbohydrate, protein, fat, and calories. Caffeine intake was controlled and maintained at the same level throughout the study. The amount of caffeine intake allowed for each individual was based on the levels of intake prior to the study. Alcohol intake was prohibited. Serum nicotine/cotinine samples were obtained at noon throughout the study. On days 2 and 6, blood samples were obtained to measure corticosteroids. On days 7 and 10, routine lab tests were taken. An internist monitored the subjects for a period of 30 minutes after the subjects took the medication to assess for any signs of toxicity.

Subjects were exposed to smoking related cues on Days 2, 5 and 9 since tobacco withdrawal symptoms may be minimized in an inpatient hospital setting when all normal cues for smoking are minimal. This cue involved exposure to their own brand of cigarettes and ashtray. Subjects were asked to look at their cigarettes, ashtray and matches for 15 seconds, light their cigarettes for 5 seconds, observe their lit cigarettes for another 15 seconds, then extinguish their cigarettes. During the study, subjects are free to engage in activities provided by the unit. Their exposure to smoking related stimuli were minimized during these activities in order to maintain consistency in cue exposures across subjects.

(S)-Cotinine was synthesized and converted into its fumarate salt by the method of McKennis and Bowman, Biochemical Preparation, 1963, 10, 36 (1963). The crystalline material was purified and found to be greater than 98% pure with no nicotine contamination. This material was characterized by elemental analysis, proton and carbon NMR, gas chromatography, and DSC. The drug substance was formulated into capsule dosage form at the Research Pharmacy at the University of Minnesota. The doses prepared were placebo (0 mg) and 40 mg, 80 mg, and 160 mg of cotinine fumarate. These were tested for uniformity of content, stability and drug release rate by standard USP dissolution testing. The doses were coded to assure a double blind clinical experiment and provided to the research staff as needed.

Statistical Analysis

Only results on selective withdrawal measures will be reported and the data should be considered preliminary. Demographic and smoking history variables were analyzed using oneway analysis of variance for continuous measures and chi square tests for categorical measures. When the between groups analysis of variance indicated a significant difference, multiple comparisons between treatment groups were performed using Tukey's HSD to determine which of the groups were significantly different from each other.

For the total withdrawal symptom score, a reliability analysis of the scale using Cronbach's alpha indicated that the craving and increased appetite items were not highly correlated with the other items on the scale. Consequently, these items were eliminated in the computation of the total withdrawal symptom score to increase the internal consistency of the scale.

The primary statistical analysis for the present study was performed using unbalanced repeated measure analysis. A between groups analysis comparing differences in withdrawal by treatment condition was conducted for all available subjects. Due to baseline differences between groups, cotinine level and number of cigarettes smoked daily were used as covariates in the analysis. Likelihood radio tests and Wald tests were used to determine the significance of each term in the model.

A. Effect of Cotinine on cigarette withdrawal. A repeated measures analysis was performed for the three days the subject was on medication. In addition to cotinine level and number of cigarettes smoked daily, the average score of the two baseline smoking days was used as covariate. For continuous measures, terms included in the regression model were an intercept, the three covariates, main effects for time of day, day on medication, medication dosage, and interaction of day on medication by medication dosage. For categorical measures, terms included in the logit or probit model were an intercept, the three covariates, main effects for time of day, medication dosage and day on medication.
Results A. Demographics, smoking history and cotinine levels. Thirty-seven subjects entered the study and 35 subjects completed the study. Two of the subjects were discharged prior to assignment to the medication. One subject experienced family problems while on the unit, and the other experienced a reoccurrence of an ulcer. Nine subjects completed the protocol in each group except the 160 mg group, in which 8 subjects completed the study. The demographic and smoking history variables are shown in Table 3.

TABLE 3

| Variable | Dose | | | | P value |
|---|---|---|---|---|---|
| | Placebo | 40 mg | 80 mg | 160 mg | |
| Females | 55.6 | 55.6 | 55.6 | 50.0 | |
| Age | 27.3 | 26.6 | 30.9 | 33.8 | .05 |
| Number of Cigarettes | 23.0 | 26.6 | 28.3 | 33.8 | .02 |
| Years of Smoking | 11.4 | 11.0 | 15.4 | 20.3 | .02 |
| Fagerstrom Score | 5.3 | 6.6 | 6.2 | 6.9 | .04 |
| Serum Cotinine | 228.4 | 288.1 | 263.9 | 350.2 | .00 |

Significant differences were observed in age, number of cigarettes, years of smoking, Fagerstrom Tolerance Questionnaire Score, and serum cotinine. Post hoc analyses showed significant differences between the 160 mg and placebo groups. Due to these differences among groups, cotinine level in mg/ml serum (shown in previous studies to be correlated with nicotine withdrawal symptoms) and number of cigarettes (which showed significant correlations with the other variables showing significant differences between treatment groups) were used as covariates. FIG. 2 shows the mean cotinine level attained for each of the three days on the medication. Significant differences were observed across the doses of cotinine ($p<0.001$).

B. Safety of cotinine. No adverse effects were noted by the subjects that would warrant termination from the study. Ten subjects, however, experienced elevated liver function tests with 4 of these subjects in the placebo group, 1 subject in the 40 mg group, 3 subjects in the 80 mg group, and 2 subjects in the 160 mg group. Two subjects (one in the 40 mg and 80 mg group) were considered to have clinically insignificant elevations. For the 6 out of 8 subjects who complied with the follow-up visit(s) to obtain repeat liver function tests, the levels had decreased to normal.

C. Effect of cotinine on cigarette withdrawal symptoms.

1. Subjective effects:

FIGS. 3–7 show the cigarette withdrawal symptoms that showed significant differences across groups. For irritability/frustration/anger (FIG. 3), anxiety (FIG. 4), difficulty concentrating (FIG. 5) and impatience (FIG. 6), the 80 mg dose group scored experienced significantly less severe symptoms than the placebo group. For irritability, the odds were 2.6 times greater to experience no irritability than slight irritability, and 6.9 times greater to experience no irritability than mild to severe irritability. For anxiety, the odds were 2.6 times greater to experience no anxiety than any anxiety. For difficulty concentrating, the odds were 4.3 times greater in experiencing no difficulty than to experience slight difficulty in concentrating and 18.5 times greater in experiencing no difficulty concentrating than to experience mild to severe difficulty concentrating. For impatience, the odds were 13.7 times greater to experience no impatience than to experience any impatience.

Figure 8:
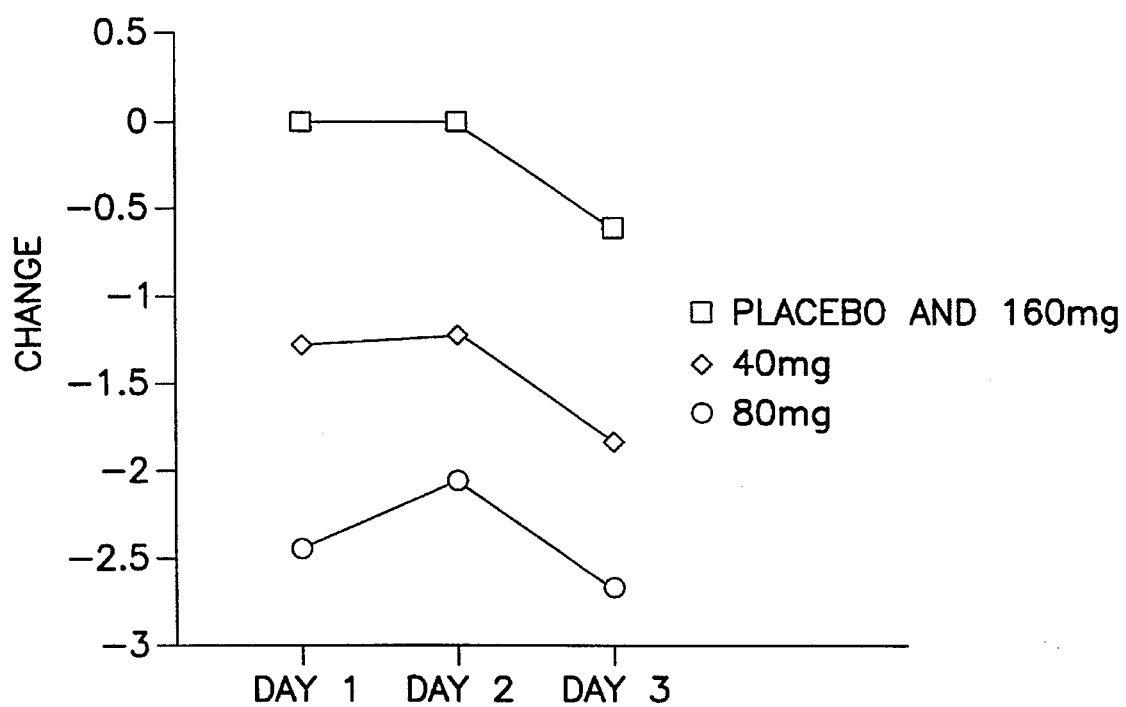
FIG. 8 is a graph depicting the change in the total withdrawal symptom score.

For increased appetite (FIG. 7) and total withdrawal score (FIG. 8), the 40 and 80 mg groups experienced significantly lower scores than placebo. For increased appetite, in the 40 mg condition, the odds were 2.7, 7.2 and 19.2 times greater in reporting no increased appetite than to have experienced slight, mild or moderate to severe increases in appetite, respectively. In the 80 mg condition, the odds were 2.8, 7.9, and 22.4 times greater in experiencing no increased appetite than to have experienced slight, mild or moderate to severe increase in appetite, respectively. The results for the total withdrawal score showed that there was a significant dose effect ($p<0.007$), with the 40 mg ($p=0.012$) and 80 mg ($p<0001$) dose groups reported experiencing significantly lower composite withdrawal syndromes than placebo. No significant differences were observed across doses for craving, restlessness and depressed mood, or for the two main factors measured by the Smoking Urges Questionnaires. No significant differences were observed for caloric intake and specific macro nutrients.

2. Physiological effects:

No significant effects of cotinine were observed for any of the physiological measures (heart rate, systolic and diastolic blood pressure).

3. Effects of cotinine during cue exposure:

No significant effects of cotinine were observed for any of the physiological (heart rate, systolic and diabolic blood pressure) and subjective withdrawal measures assessed during cue exposure conditions.

All publications and patents are herein incorporated by reference to the same extent as if each individual publication or patent was specifically and individually indicated to be incorporated by reference.

What is claimed is:

1. A pharmaceutical composition useful to assist in the cessation of smoking comprising an amount of cotinine or a pharmaceutically acceptable salt thereof sufficient to deliver a dose of cotinine to a human subject of from about 1.0 mg/kg to about 100 mg/kg in combination with a pharmaceutically acceptable carrier.

2. The composition of claim 1 wherein the cotinine is (−)-cotinine.

3. The composition of claim 2 wherein the cotinine is a salt of (−)-cotinine.

4. The composition of claim 1 which is a pharmaceutical unit dosage form.

5. The composition of claim 4 wherein the pharmaceutical unit dosage form is adapted to oral administration.

6. The composition of claim 5 wherein the pharmaceutical unit dosage form is a chewing gum.

7. The composition of claim 4 wherein the pharmaceutical unit dosage form is adapted to parenteral administration.

8. The composition of claim 7 wherein the pharmaceutical unit dosage form comprises a transdermal delivery system.

9. The composition of claim 7 wherein the pharmaceutical unit dosage form is adapted to intraocular administration.

10. The composition of claim 9 wherein the pharmaceutical unit dosage form is an intraocular insert.

11. The composition of claim 7 wherein the pharmaceutical unit dosage form is adapted to intravenous administration.

12. The composition of claim 11 which comprises cotinine or the cotinine salt dissolved in a liquid vehicle.

13. The composition of claim 7 wherein the pharmaceutical unit dosage form is adapted to intranasal administration.

14. The composition of claim 7 wherein the pharmaceutical unit dosage form is adapted to administer the cotinine or the cotinine salt by inhalation.

15. A unit dosage form useful to assist in the cessation of smoking comprising about 40 mg to about 1000 mg of cotinine in combination with a pharmaceutically acceptable carrier.

16. A pharmaceutical composition useful to maintain tobacco abstinence comprising an amount of cotinine or a pharmaceutically acceptable salt thereof sufficient to deliver a dose of cotinine to a human subject of from about 0.4 mg/kg to about 15 mg/kg in combination with a pharmaceutically acceptable carrier.

17. A unit dosage form useful to maintain tobacco abstinence comprising about 40 mg to about 1000 mg of cotinine in combination with a pharmaceutically acceptable carrier.

18. A pharmaceutical composition useful to alleviate the craving associated with the cessation of tobacco smoking comprising an amount of cotinine or a pharmaceutically acceptable salt thereof sufficient to deliver a dose of cotinine to a human subject of from about 0.4 mg/kg to about 15 mg/kg in combination with a pharmaceutically acceptable carrier, which amount is effective to alleviate craving for at least one of cigarettes, tobacco or nicotine.

19. A unit dosage form useful to alleviate the craving associated with the cessation of tobacco smoking comprising about 40 mg to about 1000 mg of cotinine in combination with a pharmaceutically acceptable carrier.

* * * * *